United States Patent
Dufort et al.

(10) Patent No.: US 10,307,352 B2
(45) Date of Patent: Jun. 4, 2019

(54) LOW OIL COMPOSITIONS COMPRISING A 4-SUBSTITUTED RESORCINOL AND A HIGH CARBON CHAIN ESTER

(71) Applicant: Johnson & Johnson Consumer Inc., Skillman, NJ (US)

(72) Inventors: Marisa DeVita Dufort, Hillsborough, NJ (US); Simarna Kaur, Neschanic Station, NJ (US); Michael D. Southall, Pennington, NJ (US); Ping Wen, Belle Mead, NJ (US); Jeffrey M. Wu, Princeton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/251,121

(22) Filed: Aug. 30, 2016

(65) Prior Publication Data

US 2016/0367452 A1    Dec. 22, 2016

Related U.S. Application Data

(63) Continuation of application No. 13/624,998, filed on Sep. 24, 2012, now abandoned.

(51) Int. Cl.

| | |
|---|---|
| *A61K 8/37* | (2006.01) |
| *A61K 8/34* | (2006.01) |
| *A61Q 19/02* | (2006.01) |
| *A61Q 19/08* | (2006.01) |
| *A61K 8/81* | (2006.01) |

(52) U.S. Cl.
CPC ............ *A61K 8/347* (2013.01); *A61K 8/345* (2013.01); *A61K 8/37* (2013.01); *A61K 8/8147* (2013.01); *A61K 8/8152* (2013.01); *A61K 8/8182* (2013.01); *A61Q 19/02* (2013.01); *A61Q 19/08* (2013.01); *A61K 2800/30* (2013.01)

(58) Field of Classification Search
None
See application file for complete search history.

(56) References Cited

U.S. PATENT DOCUMENTS

| | | |
|---|---|---|
| 1,649,670 A | 11/1927 | Dohme |
| 2,697,118 A | 12/1954 | Lundsted et al. |
| 3,193,507 A | 7/1965 | Jacobs |
| 4,093,667 A | 6/1978 | Starks |
| 4,337,370 A | 6/1982 | Takisawa et al. |
| 4,959,393 A | 9/1990 | Torihara et al. |
| 5,116,604 A | 5/1992 | Fogel et al. |
| 5,227,459 A | 7/1993 | Pawelek et al. |
| 5,384,116 A | 1/1995 | Pawelek et al. |
| 5,618,519 A | 4/1997 | Pawelek et al. |
| 5,705,145 A | 1/1998 | Miklean et al. |
| 5,840,285 A | 11/1998 | Fogel |
| 5,841,285 A | 11/1998 | Bailey |
| 6,113,926 A | 9/2000 | Soler et al. |
| 6,264,964 B1 | 7/2001 | Mohammadi |
| 6,322,766 B1 | 11/2001 | Ortega, II et al. |
| 6,322,776 B1 | 11/2001 | Ortega, II et al. |
| 6,528,043 B2 | 3/2003 | Rubinstenn et al. |
| 6,797,697 B2 | 9/2004 | Seiberg et al. |
| 6,852,310 B2 | 2/2005 | Harichian et al. |
| 6,858,217 B2 | 2/2005 | Kerschner et al. |
| 6,863,897 B2 | 3/2005 | Love et al. |
| 6,869,598 B2 | 3/2005 | Love et al. |
| 6,890,519 B2 | 5/2005 | Mercier et al. |
| 6,926,886 B2 | 8/2005 | Lin et al. |
| 7,025,951 B2 | 4/2006 | Seiberg et al. |
| 7,214,655 B2 | 5/2007 | Seiberg et al. |
| 7,442,391 B2 | 10/2008 | Koganov |
| 7,468,464 B2 | 12/2008 | Harichian et al. |
| 7,473,435 B2 | 1/2009 | Koganov |
| 7,537,791 B2 | 5/2009 | Koganov |
| 8,084,504 B2 | 12/2011 | Johnson et al. |
| 8,318,217 B2 | 11/2012 | Kaur et al. |
| 8,425,941 B2 | 4/2013 | Yagi et al. |
| 2002/0182166 A1 | 12/2002 | Martin et al. |
| 2003/0003170 A1 | 1/2003 | Callaghan et al. |
| 2003/0180234 A1 | 9/2003 | Love et al. |
| 2004/0009200 A1 | 1/2004 | Seyler et al. |
| 2004/0109832 A1 | 6/2004 | Harichian et al. |
| 2004/0156873 A1 | 8/2004 | Gupta |
| 2005/0048008 A1 | 3/2005 | Gupta |
| 2006/0019002 A1 | 1/2006 | Xue |
| 2006/0088608 A1 | 4/2006 | Seiberg et al. |
| 2006/0120975 A1 | 6/2006 | Scherl et al. |
| 2006/0210497 A1 | 9/2006 | Harichian et al. |

(Continued)

FOREIGN PATENT DOCUMENTS

| | | |
|---|---|---|
| CN | 102573820 A | 7/2012 |
| DE | 10118894 A1 | 10/2002 |

(Continued)

OTHER PUBLICATIONS

Alzo International Inc., Technical Bulletin # 0622, Elefac I-205, available prior to Sep. 24, 2012.
Colipa Guideline: Guideline for the Colorimetric Determination of Skin Colour Typing and Prediction of the Minimal Erythemal Dose (MED) without UV Exposure, published 2007.
Dow Corning(R) 344 Fluid Safety Data Sheet, accessed Mar. 28, 2016.
European Search Report for corresponding application No. EP 13185624.7 dated Feb. 17, 2014.
Pemulen™ TR-2—product page from Lubrizol, accessed Mar. 28, 2016.
Shaath, "SPF Boosters & Photostability of Ultraviolet Filters", published Oct. 1, 2007 www.happi.com/contents/view_features/2007-10-01/spf-boosters--photostability-of-ultraviolet-f.

(Continued)

*Primary Examiner* — Nissa M Westerberg

(57) ABSTRACT

A composition including water, about 0.1% to about 0.4% of a 4-substituted resorcinol, an ester having at least about 25 carbon atoms, and a polymeric emulsifier is provided. The composition comprises less than about 5% by weight of oils and is substantially free of monomeric emulsifier. Methods of treating the skin are also provided.

3 Claims, No Drawings

(56) References Cited

U.S. PATENT DOCUMENTS

| | | | |
|---|---|---|---|
| 2006/0239945 | A1 | 10/2006 | Bapat et al. |
| 2006/0264497 | A1 | 11/2006 | Zeligs |
| 2006/0269504 | A1 | 11/2006 | James |
| 2006/0292184 | A1 | 12/2006 | Richardson et al. |
| 2007/0003536 | A1 | 1/2007 | Zimmerman et al. |
| 2007/0042010 | A1 | 2/2007 | Southall et al. |
| 2007/0098655 | A1 | 5/2007 | Schmaus et al. |
| 2007/0184017 | A1 | 8/2007 | Faryniarz et al. |
| 2007/0196523 | A1 | 8/2007 | Koganov |
| 2008/0026974 | A1 | 1/2008 | Barnhart et al. |
| 2008/0095719 | A1 | 4/2008 | Herrmann et al. |
| 2008/0131382 | A1 | 6/2008 | Harichian et al. |
| 2008/0249029 | A1 | 10/2008 | Shapiro et al. |
| 2008/0260671 | A1 | 10/2008 | De La Torre et al. |
| 2008/0286217 | A1 | 11/2008 | Chaudhuri |
| 2008/0305059 | A1 | 12/2008 | Chaudhuri |
| 2008/0317887 | A1 | 12/2008 | Mitchell et al. |
| 2009/0087395 | A1 | 4/2009 | Lin et al. |
| 2009/0181926 | A1 | 7/2009 | Akamatsu et al. |
| 2009/0252758 | A1 | 10/2009 | Mazed et al. |
| 2009/0253663 | A1 | 10/2009 | Akamatsu et al. |
| 2009/0263513 | A1 | 10/2009 | Marini |
| 2009/0286749 | A1* | 11/2009 | Roberto .................. A61K 8/37 514/23 |
| 2010/0124539 | A1 | 5/2010 | Hanson |
| 2010/0189669 | A1 | 7/2010 | Hakozaki et al. |
| 2010/0291014 | A1 | 11/2010 | Tellefsen et al. |
| 2011/0081305 | A1 | 4/2011 | Cochran et al. |
| 2011/0081430 | A1 | 4/2011 | Kaur et al. |
| 2011/0081431 | A1 | 4/2011 | Kaur et al. |
| 2011/0081433 | A1 | 4/2011 | Kaur et al. |
| 2011/0082217 | A1* | 4/2011 | Johnson ................ A61K 8/347 514/731 |
| 2011/0171288 | A1 | 7/2011 | Mohammadi et al. |
| 2011/0213030 | A1 | 9/2011 | Shinto et al. |
| 2012/0064149 | A1 | 3/2012 | Johnson et al. |
| 2012/0101156 | A1 | 4/2012 | Oddos |
| 2012/0128605 | A1 | 5/2012 | Cochran et al. |
| 2012/0128613 | A1 | 5/2012 | Cochran et al. |
| 2012/0177587 | A1 | 7/2012 | Daubresse et al. |
| 2013/0071453 | A1 | 3/2013 | Sojka et al. |
| 2013/0162992 | A1 | 6/2013 | Schmidt et al. |
| 2013/0164393 | A1 | 6/2013 | Kaur et al. |
| 2013/0165512 | A1 | 6/2013 | Oddos |
| 2013/0171219 | A1 | 7/2013 | Johnson et al. |
| 2013/0171281 | A1 | 7/2013 | Kaur et al. |
| 2013/0202546 | A1 | 8/2013 | Howell et al. |
| 2014/0086859 | A1 | 3/2014 | Dufort et al. |
| 2015/0064292 | A1 | 3/2015 | Kaur et al. |
| 2015/0272837 | A1 | 10/2015 | Brillouet et al. |

FOREIGN PATENT DOCUMENTS

| | | |
|---|---|---|
| DE | 10157490 A1 | 6/2003 |
| EP | 0341664 A1 | 11/1989 |
| EP | 1250908 A2 | 10/2002 |
| EP | 1348418 A1 | 10/2003 |
| EP | 1299069 B1 | 12/2005 |
| EP | 1974773 A2 | 10/2008 |
| EP | 1987811 A2 | 11/2008 |
| EP | 2036565 A1 | 3/2009 |
| EP | 2045297 A2 | 4/2009 |
| EP | 2100593 A1 | 9/2009 |
| EP | 2316412 A2 | 5/2011 |
| EP | 2674146 A1 | 12/2013 |
| FR | 2746008 A1 | 9/1997 |
| GB | 821726 A | 10/1959 |
| GB | 2438999 A | 12/2007 |
| IN | 188649 B | 10/2002 |
| JP | H11100324 A | 4/1999 |
| JP | 2000327557 A | 11/2000 |
| JP | 2001010925 A | 1/2001 |
| JP | 2001302505 A | 10/2001 |
| JP | 2004107210 A | 4/2004 |
| JP | 2006327965 A | 12/2006 |
| JP | 2006327967 A | 12/2006 |
| JP | 2007254412 A | 10/2007 |
| JP | 4004182 B2 | 11/2007 |
| JP | 2007332116 A | 12/2007 |
| JP | 2008184431 A | 8/2008 |
| JP | 2009084164 A | 4/2009 |
| KR | 20030089598 A | 11/2003 |
| WO | WO-9853822 A1 | 12/1998 |
| WO | WO-0189502 A2 | 11/2001 |
| WO | WO-02074280 A1 | 9/2002 |
| WO | WO-03080009 A1 | 10/2003 |
| WO | WO-03082231 A2 | 10/2003 |
| WO | WO-2004052330 A1 | 6/2004 |
| WO | WO-2004062637 A1 | 7/2004 |
| WO | WO-2004105736 A1 | 12/2004 |
| WO | WO-2006097223 A1 | 9/2006 |
| WO | WO-2006128032 A2 | 11/2006 |
| WO | WO-2007021240 A1 | 2/2007 |
| WO | WO-2008143761 A1 | 11/2008 |
| WO | WO-2008148016 A1 | 12/2008 |
| WO | WO-2008153629 A1 | 12/2008 |
| WO | WO-2009067095 A1 | 5/2009 |
| WO | WO-2009145300 A1 | 12/2009 |
| WO | WO-2010072787 A2 | 7/2010 |

OTHER PUBLICATIONS

Akerlof, "Dielectric Constants of Some Organic Solvent-Water Mixtures at Various Temperatures," The Journal of the American Chemical Society, Nov. 1932, vol. 54(11), pp. 4125-4139.

Belikov, V.G., "Pharmaceutical Chemistry", 1993, vol. 1, pp. 43-47.

Bobin, M., et al., "Effects of Color Adjuvants on the Tanning Effect of Dihydroxyacetone", Journal of the Society Cosmetology Chemistry, Aug. 1984, vol. 35, pp. 265-272.

Cenizo, V., et al., "LOXL as a Target to Increase the Elastin Content in Adult Skin: A Dill Extract Induces the LOXL Gene Expression," Experimental Dermatology, Aug. 2006, vol. 15(8), 574-581.

Database GNPD [Online] Mintel; Feb. 2009, "Advanced Luminescence Serum", Database accession No. 1060752.

Database GNPD [Online] Mintel; Jan. 2004, "Max Strength Sore Throat Relief Lozenges", XP002695248, Database accession No. 252009.

Database GNPD [Online] Mintel; Jun. 2009, "Instant Facial Sculpting", Database accession No. 1123303.

Database GNPD [Online] Mintel; Jun. 30, 2008, "Enlighten Facial Lotion", XP002708108, Database Aaccession No. 925294, Abstract.

Database GNPD [Online] Mintel: Mar. 2009, "Facial Serum", XP002695055, Database accession No. 1076327.

Database GNPD [Online] Mintel; May 2008, "Anti-oxidant Bio Moisturizing Cream SPF 15", XP002695056, Database accession No. 914469.

Database GNPD [Online] Mintel: Oct. 2008, "Eye Recovery", XP002695054, Database accession No. 992121.

Database WPI Week 199637 Thomson Scientific, London, GB; AN1996-368117, XP002625251, & JPH08176004A (Lion Corp) Jul. 9, 1996, Abstract.

Database WPI, Week 200223, Thomson Scientific, London, GB; AN 2002-174418 XP002635474, JP200130205A (Kurarray Co Ltd) Oct. 31, 2001, Abstract.

Fukuda, K., et al., "Inhibition by Parthenolide of Phorbol Ester-induced Transcriptional Activation of Inducible Nitric Oxide Synthase Gene in a Human Monocyte Cell Line THP-1," Biochemical Pharmacology, Aug. 2000, vol. 60(4), pp. 595-600.

Hall, et al., "The Solubilization of Hexylresorcinol by an Anionic-Nonionic Surfactant Mixture," American Journal of Pharmacy and the Sciences Supporting Public Health, Nov.-Dec. 1966, vol. 138(6), pp. 245-248.

Hamamoto, Y., et al., "Inhibitory Effect of Azelastine, a Potent Antiallergic Agent, on Release of Tumor Necrosis Factor-alpha from Activated Human Peripheral Blood Mononuclear Cells and U937 Cells," Experimental Dermatology, Oct. 1993, vol. 2(5), pp. 231-235.

(56) References Cited

OTHER PUBLICATIONS

Herrmann, et al., "Blackberry Leaf Extract A New Anti-Aging Active," SOFW Journal, 2006, vol. 132(4), pp. 42-46.

International Cosmetic Ingredient Dictionary and Handbook, eds. Pepe, Wenninger and McEwen, (The Cosmetic, Toiletry, and Fragrance Assoc., Washington, D.C., 9th Edition, 2002), pp. 2930-2936, pp. 2962-2971, pp. 2979-2984.

Kaur et aL, "4-Hexyl-1,3-phenylenediol, a Nuclear Factor-κB Inhibitor, Improves Photodamaged Skin and Clinical Signs of Ageing in a Double-blinded, Randomized Controlled Trial," British Journal of Dermatology, Jul. 2015, vol. 173(1), pp. 218-226.

Kolbe et al., "4-n-butylresorcinol, a Highly Effective Tyrosinase Inhibitor for the Topical Treatment of Hyperpigmentation," Journal of the European Academy of Dermatology and Venereology, Jan. 2013, vol. 27(Suppl. 1), pp. 19-23.

Lamaison, J.L., et al., "Tannin Content and Elastase Inhibiting Activity in the Rosaceae Family," Annales Pharmaceutiques Francaises, Jan. 1990, vol. 48(6), pp. 335-340.

Lin, et al., "Theaflavin-3,3'-digallate from Black Tea Blocks the Nitric Oxide Synthase by Down-regulating the Activation of NF-kappaB in Macrophages," European Journal of Pharmacology, Feb. 1999, vol. 367(2-3), pp. 379-388.

Liu, B., et al., "Retinoic Acid Increases Elastin in Neonatal Rat Lung Fibroblast Cultures," The American Journal of Physiology, Nov. 1993, vol. 265(5pt. 1), pp. L430-L437.

Liu, X., et al., "Elastic Fiber Homeostasis Requires Lysyl Oxidase-like 1 Protein," Nature Genetics, Feb. 2004, vol. 36(2), pp. 178-182.

Ochsner, A.B. and Sokoloski, T.D., "Prediction of Solubility in Nonideal Multicomponent Systems Using the UNIFAC Group Contribution Model," Journal of Pharmaceutical Sciences, Jun. 1985, vol. 74(6), pp. 634-637.

Prakash, et al., "Multifunctional Ingredients: the Novel Face of Natural" in Antiaging: physiology to formulation, 2006, pp. 181-188.

Product Scan Information: Jan Marini Age Intervention Enlighten, 2008/2009.

Product Scan Information: Kinerase—Brightening Anti-Aging System, 2008/2009.

Staal, F. J., et al., "Antioxidants Inhibit Stimulation of HIV Transcription", Aids Research and Human Retroviruses, Jan. 1993, vol. 9(4), pp. 299-306.

Suzuki, Y. J., et al., "Inhibition of NF-kappaB Activation by Vitamin E Derivatives", Biochemical and Biophysical Research Communications, May 1993, vol. 193(1), pp. 277-283.

Xia, et al., "Dehydration of Ethyl Acetate-water Mixtures using PVA/ceramic Composite Pervaporation Membrane," Separation and Purification Technology, Feb. 2011, vol. 77(1), pp. 53-59.

* cited by examiner

LOW OIL COMPOSITIONS COMPRISING A 4-SUBSTITUTED RESORCINOL AND A HIGH CARBON CHAIN ESTER

CROSS-REFERENCE TO RELATED APPLICATIONS

This application is a continuation of U.S. patent application Ser. No. 13/624,998 filed Sep. 24, 2012, the disclosure of which is incorporated by reference in its entirety.

FIELD OF THE INVENTION

A low oil composition comprising a 4-substituted resorcinol, a high carbon chain ester and a cosmetically acceptable topical carrier is provided. The composition is useful for topical application to the skin.

BACKGROUND OF THE INVENTION

4-Substituted resorcinols are known to provide anti-aging and lightening benefits to the skin when applied topically. For various reasons, such as cost and formulation integrity it is desirable to reduce the concentration of 4-substituted resorcinols in topical skin products. However, reducing the concentration of 4-substituted resorcinols can also reduce the observed benefit. Accordingly, the inventors have recognized the need for formulations with reduced concentrations of 4-substituted resorcinols. Surprisingly, the inventors have found that low oil compositions that include a high carbon chain ester can be formulated with low concentrations of 4-substituted resorcinols and still provide skin benefits.

SUMMARY OF THE INVENTION

In one aspect, the invention provides a composition including water, about 0.1% to about 0.4% of a 4-substituted resorcinol, an ester having at least about 25 carbon atoms, and a polymeric emulsifier. The composition comprises less than about 5% by weight of oils and is substantially free of monomeric emulsifier. Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

Compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

Compositions of the present invention are suitable for treating acne. As used herein, "treating acne" refers to a mitigating, reducing, preventing, improving, or eliminating the presence or signs of disorders resulting from the actions of hormones and other substances on the sebaceous glands and hair follicles, typically leading to clogged pores and the formation of lesions on the skin.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

4-Substituted Resorcinols

Compositions of the present invention comprise a 4-substituted resorcinol. 4-Substituted resorcinols have the chemical structure of resorcinol but include a substitution at the 4 position. Suitable 4-substituted resorcinols include those having alkyl, aryl, alkenyl, or alkynyl substitutions. In one embodiment, the 4-substituted resorcinol comprises a C4-C10 substitution. In certain embodiments the other positions may be substituted or unsubstituted.

In one embodiment, the 4-substituted resorcinol is 4-hexyl resorcinol, which has the following structure:

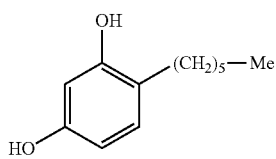

4-hexyl resorcinol is commercially available, for example, as "SYNOVEA HR" from Sytheon of Lincoln Park, N.J.

The inventors have found that topical compositions according to invention comprising low levels of 4-substituted resorcinols provide surprisingly good efficacy for skin benefits such as anti-aging, anti-acne, and lightening benefits. Specifically, the compositions comprise about 0.1% to about 0.4% by weight of 4-substituted resorcinol. In certain embodiments the compositions comprise about 0.2% to about 0.4%, such as from about 0.3% to about 0.4%, by weight of 4-substituted resorcinol. One or more than one 4-substituted resorcinol may be used.

High Carbon Chain Ester

Compositions of the present invention include a high carbon chain ester, i.e., an ester having at least about 25 carbon atoms. The inventors have found that inclusion of a high carbon chain ester in the compositions tends to improve dramatically the activity of 4-substituted resorcinol. Suitable high carbon chain esters are generally hydrophobic and include those having, for example from 25 to about 100 carbon atoms, such as those having from 25 to about 75 carbon atoms, such as those having from 25 to about 50 carbon atoms, such as those having from 25 to 37 carbon atoms. One or more than one high carbon chain ester may be used.

In one embodiment, the high carbon chain ester is branched.

In another embodiment, the high carbon chain ester is a liquid at room temperature and atmospheric pressure and may have a melting point less than 30° C., such as less than 25° C.

In another embodiment, the high carbon chain ester has from one to four ester groups.

The high carbon chain ester is desirably non-ionic and free of hydrophilic moieties (e.g., anionic, cationic, zwitterionic, or nonionic groups that are polar, including sulfate, sulfonate, carboxylate, phosphate, phosphonates, ammonium, including mono-, di-, and trialkylammonium species, pyridinium, imidazolinium, amidinium, poly(ethyleneiminium), ammonioalkylsulfonate, ammonioalkylcarboxylate, amphoacetate, hydroxyl, and poly(ethyleneoxy)sulfonyl) that would otherwise tend to render the ester amphiphilic.

Further, the high carbon chain ester is desirably composed of only hydrogen, carbon, and oxygen atoms and may be free of ether functional groups.

Specific examples of suitable high carbon chain esters include octyldodecyl neopentanoate, a C25 ester that is commercially available as ELEFAC I-205 from Alzo International Inc. of Sayerville, N.J.; and pentaerythritol tetra-ethylhexanoate, a C37 ester that is commercially available as DUB PTO also from Alzo International Inc. of Sayerville, N.J.

The amount of the high carbon chain ester in the composition may range, for example, from about 0.1% to about 5% by weight of the composition. In certain embodiments the high carbon chain ester is present in an amount of about 0.1% to about 3%, such as from about 1% to about 3%, by weight of the composition.

Polymeric Emulsifier

Compositions of the present invention include a polymeric emulsifier (i.e., having one or more definable repeat unit). In certain embodiments, the repeat unit is other than oxyalkylene ($-C_nO-$) where n is from 1 to 5. The polymeric emulsifier is suitable for emulsifying discrete oil-phase droplets in a continuous water phase or vice-versa. Specifically, a mixture that is visibly homogeneous results when 0.25% to 2% by weight of the polymeric emulsifier is mixed, either lightly or vigorously, with 1% by weight mineral oil in either pure deionized water or deionized water whose pH has been adjusted into the range of 5-10 with either HCl or NaOH. By "visibly homogeneous," it is meant that the mixture is rendered phase stable by preventing any evident "layering," flotation, or visible phase separation at room temperature and pressure for a period of at least one week and preferably at least one month.

Polymeric emulsifiers useful in the present invention may have a weight average molecular weight that is greater than about 1000 daltons, such as greater than about 5000 daltons. In certain cases, polymeric emulsifiers useful in the present invention are fully cross-linked and therefore have an infinite molecular weight.

Polymeric emulsifiers include, for example, hydrophobically-modified, crosslinked, anionic acrylic copolymers, including random polymers, but may also exist in other forms such as block, star, graft, and the like.

In one embodiment, the hydrophobically modified, crosslinked, anionic acrylic copolymer may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least about 3 carbon atoms. An example of a suitable hydrophobically modified acrylic polymer is an acrylates/C10-30 alkyl acrylate crosspolymer, such as PEMULEN TR-1 available from Lubrizol Corporation of Ohio.

According to other embodiments, the polymeric emulsifier is a water-soluble or water-swellable copolymer based on acrylamidoalkyl sulfonic acid and cyclic N-vinylcarboxamides such as commercially available ARISTOFLEX® AVC by Clariant Corporation; a water-soluble or water-swellable copolymer based on acrylamidoalkyl sulfonic acid and hydrophobically modified methacrylic acid such as commercially available ARISTOFLEX® HMB by Clariant Corporation; or a homopolymer of acrylamidoalkyl sulfonic acid such as commercially available Granthix APP by Grant Industries, Inc. According to other embodiments, the polymeric emulsifier is an ethylcellulose polymer.

The amount of polymeric emulsifier in the composition may range, for example, from about 0.1% to about 5% by weight of the composition. In certain embodiments, the amount of polymeric emulsifier is about 0.25% to about 3%, such as from about 0.5% to about 1%, by weight of the composition. One or more than one polymeric emulsifier may be used.

Low-Oil

Although compositions of the present invention include a high carbon chain ester, they are nevertheless low oil compositions. By "low oil" it is meant that the amount of oils in the composition is not excessive; in particular the total amount of oils (inclusive of the high carbon chain ester) in the composition is less than about 5% by weight of the composition.

As used herein, "oils" means hydrophobic compounds including hydrocarbon oils such as mineral oils, petrolatum, vegetable oils (e.g. triglycerides such as caprylic/capric triglyceride), and other mixtures of fatty esters, including but not limited to esters of glycerol, and high viscosity silicone oils such as those having 6 or more alkylsiloxy groups in sequence and/or those silicone oils having a viscosity of 350 centistokes or more at standard temperature and pressure. Hydrocarbon oils have a carbon chain length of at least eight, and in certain embodiments at least eleven, in which none of the carbons is a carbonyl carbon or has a hydrophilic moiety (described above with respect to the high carbon chain ester) bonded directly to it. Also encompassed in the definition of oils are compounds that meet the requirements described above and are solid at room temperature (often called "waxes"). "Oil" as described herein does not encompass those compounds having a carbon chain that requires aromatic groups to achieve the limit of at least eight or at least eleven carbons.

Monomeric Emulsifiers

Compositions of the present invention are substantially free of monomeric emulsifiers. Monomeric emulsifiers are non-polymeric compounds suitable for emulsifying discrete oil-phase droplets in a continuous water phase or vice-versa. Specifically, monomeric emulsifiers are able to render a mixture of 1% by weight mineral oil in pure deionized water phase stable. Monomeric emulsifiers may have a molecular weight that is less than 5000 daltons, such as less than 1000 daltons.

Common monomeric emulsifiers are amphiphilic molecules and may be anionic, non-ionic, cationic, or amphoteric. Anionic emulsifiers include particular molecules of various chemical classes, for example, alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates.

Nonionic emulsifiers may include, for example, amide ethoxylates, monoglyceride ethoxylates, sorbitan ester ethoxylates alkyl polyglycosides, mixtures thereof, and the like. Certain other notable nonionic emulsifiers include polyoxyethylene derivatives of polyol esters, wherein the polyoxyethylene derivative of polyol ester (1) is derived from (a) a fatty acid containing from about 8 to about 22, such as from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, such as about 20 to about 80 oxyethylene units; and (3) has an average of about 1 to about 3 fatty acid residues per mole of polyoxyethylene derivative of polyol ester, alkyl glucosides or polyglucosides, which are the condensation products of (a) a long chain alcohol containing from about 6 to about 22, such as from about 8 to about 14 carbon atoms, with (b) glucose or a glucose-containing polymer; silicone emulsifiers such as crosslinked or noncrosslinked silicone copolymers of polyethylene glycol, polypropylene glycol or polyglyceryl esters.

Amphoteric emulsifiers may include 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates.

Cationic emulsifiers include may include alkyl quaternaries (mono, di, or tri), benzyl quaternaries, ester quaternaries, ethoxylated quaternaries, alkyl amines, and the like.

As used herein, "substantially free of monomeric emulsifier" means the amount of monomeric emulsifier in the composition is insufficient to render the composition phase stable were any polymeric emulsifier removed from the composition and replaced with water. In certain other embodiments the amount of monomeric emulsifier is less than about 1% by weight of the composition. In certain other embodiments, the amount of monomeric emulsifier is less than the amount of polymeric emulsifier in the composition. In other embodiments, the composition is free of monomeric emulsifier.

Topical Compositions

The composition also includes water. In one embodiment, the composition comprises at least about 70% by weight of water.

The composition is applied topically to human skin and/or hair. The composition may further include other ingredients that may comprise about 50% to about 99.99%, by weight, of the composition (e.g., from about 80% to about 99.9%, by weight, of the composition), such as humectants, chelating agents (e.g., EDTA), pH adjusters (e.g., citric acid, sodium hydroxide), preservatives (e.g., chlorphenesin), texture aids/skin conditioners (e.g., starch polymers, cationics, and the like), low viscosity organosiloxanes, additional skin benefit agents and the like.

Suitable humectants include glycols such as glycerin, butylene glycol, propylene glycol, polyethylene glycol (n=200 to 600), polypropylene glycol (n=425 to 2025), 1,2,4-butanetriol, sorbitol esters, 1,2,6-hexanetriol, urea, and mixtures thereof. The humectants may be present in an amount of about 1% to about 20%, such as from about 2% to about 12%, such as from about 3% to about 10%, by weight of the composition.

Suitable low viscosity organosiloxanes include low viscosity dimethicone and other silicones having about 5 or less alkylsiloxy groups in sequence. Examples include DC 200 Fluid, 50 cst and DC 2-1184 from Dow Corning.

In one embodiment, the composition further contains a skin benefit agent other than 4-substituted resorcinol. As used herein, a "skin benefit agent" is a compound (e.g., a synthetic compound or a compound isolated from a natural source or a natural extract) that has a cosmetic or therapeutic effect on the skin or hair, including, but not limited to, anti-acne agents, anti-inflammatory agents external analgesics, sunscreens, antioxidants, keratolytic agents, vitamins (e.g., Vitamin D, vitamin B, Vitamin A), anti-aging actives (including skin firming agents, collagen promoters, elastin promoters, skin lighteners, and the like). The additional skin benefit agent will typically be present in the composition in an amount of about 0.001% to about 20% by weight of the composition, e.g., about 0.005% to about 10% such as about 0.01% to about 5% by weight of the composition.

The compositions of the present invention may be prepared using methodology that is well known by an artisan of ordinary skill.

Methods of Use

Compositions of the present invention may be topically applied to mammalian skin. In one embodiment, the skin is in need of treatment for one or more signs of skin aging as described above. In one embodiment, the compositions are applied to skin in need of treatment for lines and wrinkles and/or loss of elasticity. The compositions may be applied to the skin in need of such treatment according to a suitable treatment regimen, e.g., from as much as, twice per day to as little as once every three days or so.

In certain embodiments, compositions of the present invention may also be useful for treating other need states associated with skin. For example, compositions of the present invention may be useful for treating post-inflammatory hyperpigmentation, for reducing pore size, for reducing sebum production, and for scar mitigation.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example I: Preparation of Test Compositions

Composition 1 according to the invention was prepared using 4-hexyl resorcinol, octyldodecyl neopentanoate, a high carbon chain ester, and the other components in Table 1 as follows.

In a main vessel, water was charged and mixing begun. VERSENE NA and chlorphenesin were added. PEMULEN TR-1 was slowly added and mixed until dispersed. The vessel was then heated to 70-75° C. at which point OLIVEM 1000 was added and mixed until uniform. The vessel was then cooled to 60-65° C., at which point ARISTOFLEX AVC was added and mixed until completely dispersed. EUXYL PE9010 was then added and mixed until uniform. The vessel was then cooled. At 55-60° C., DC 200 Fluid 50 cst was added and mixed for 5 minutes. DC2-1184 was then added and mixed until uniform. Once the temperature reached below 40° C., the pH was adjusted to 4.9-5.2 using 20% sodium hydroxide solution. Then Advanced Moisture Complex w, NAB Mushroom, flaxseed oil, vitamin D, panthenol and fragrance were added and mixed until uniform. A premix of butylene glycol, and DRY FLO PURE was prepared by mixing until homogeneous and no lumps. This was added to the main vessel and mixed well. A 4-hexyl resorcinol premix (previously prepared by adding 4-hexyl resorcinol to glycerin under a hood, heating to 40 C and mixing until fully dissolved) was then added and mixed until uniform. ELEFAC was then added and homogenized with a Silverson homogenizer for 3 min at approx 3000 rpm.

TABLE 1

| Composition 1 | | |
|---|---|---|
| Trade name | INCI | % w/w |
| Purified Water | Water | 81.94 |
| PEMULEN TR-1 | Acrylates/C10-30 Alkyl Acrylates Copolymer | 0.08 |
| OLIVEM 1000 | Cetearyl Olivate; Sorbitan Olivate | 0.5 |
| ARISTOFLEX AVC | Ammonium Acryloyldimethyltaurate/VP Copolymer | 0.7 |
| EUXYL PE 9010 | Phenoxyethanol; Ethylhexylglycerin | 0.9 |
| DC 200 Fluid 50 cst. | Dimethicone | 2.0 |
| DC 2-1184 | Dimethicone; Trisiloxane | 4.0 |
| Advanced Moisture Complex w | Glycerin; Water; Sodium PCA; Urea; Trehalose; Polyquaternium-51; Triacetin; Sodium Hyaluronate | 1.0 |
| NAB Mushroom PF | Algae Extract; Ganoderma Lucidum (Mushroom) Stem Extract; Lentinus Edodes Extract | 0.3 |
| Paraoil Flaxseed oil | Linum Usitatissimum (Linseed) Seed Oil | 0.2 |
| Vitamin D3 1.0 Mill/g | Cholecalciferol; Caprylic/Capric Triglyceride; Tocopherol | 0.04 |
| D-Panthenol | Panthenol | 0.1 |
| Glycerin 99% USP | Glycerin | 4.0 |
| SYNOVEA HR | 4-Hexylresorcinol | 0.38 |
| 1,3-Butylene Glycol | Butylene Glycol | 2.0 |
| COSVAT | Chlorphenesin | 0.25 |
| DRY FLO PURE | Aluminum Starch Octenylsuccinate | 1.0 |
| VERSENE NA | Disodium EDTA | 0.2 |

TABLE 1-continued

Composition 1

| Trade name | INCI | % w/w |
|---|---|---|
| ELEFAC I-205 | Octyldodecyl neopentanoate | 0.1 |
| Fragrance | Fragrance | 0.3 |
| Sodium Hydroxide | Sodium Hydroxide | 0.01 |

PEMULEN TR-1 is available from Lubrizol of Wickliffe, Ohio. OLIVEM TR-1 is available from B&T Srl of Arcore, Italy. ARISTOFLEX AVC is available from Clariant Corporation Charlotte, N.C. EUXYL PE 9010 is available from Schulke & Mayr GmbH of Norderstedt, Germany. DC 200 Fluid and DC 2-1184 are available from Dow Corning of Midland, Mich. Advanced Moisture Complex w and Vitamin D3 are available from BASF of Ludwigshafen, Germany. NAB Mushroom PF is available from Arch Lonza of Basel, Switzerland. Paraoil Flaxseed Oil is available from Paradigm Science: Benxi, China. SYNOVEA HR is available from Sytheon of Lincoln Park, N.J. COVSAT is available from Vivimed labs LTD of Bonthapally Village, India. DRY-FLO PURE is available from AkzoNobel of Chicago, Ill. VERSENE NA is available from Dow Chemical of Midland, Mich. ELEFAC I-205 is octyldodecyl neopentanoate, a C25 ester that is commercially available from Alzo International Inc. of Sayerville, N.J.

Additional compositions were prepared by changing the amount of octyldodecyl neopentanoate and adjusting with water, or replacing the octyldodecyl neopentanoate with a different ester. The compositions are listed in Table 2. Compositions 2-6 were according to the invention (Compositions 3 and 4 both contained 3% octyldodecyl neopentanoate). Comparative Compositions C1-C4 did not contain a high carbon chain ester.

TABLE 2

| Composition | Ester |
|---|---|
| Comparative Composition C1 (control) | None |
| Composition 1 | 0.1% octyldodecyl neopentanoate |
| Composition 2 | 1% octyldodecyl neopentanoate |
| Composition 3 | 3% octyldodecyl neopentanoate |
| Composition 4 | 3% octyldodecyl neopentanoate |
| Composition 5 | 10% octyldodecyl neopentanoate |
| Composition 6 | 3% pentaerythritol tetraethylhexanoate |
| Comparative Composition C2 | 3% neopentyl glycol diheptanoate |
| Comparative CompositionC3 | 3% C12-C15 alkyl benzoate |
| Comparative Composition C4 | 3% isononyl isononanoate |

Pentaerythritol tetraethylhexanoate was obtained as DUB PTO, a C37 ester commercially available from Alzo International Inc. of Sayerville, N.J. 7 Neopentyl glycol diheptanoate was obtained as LEXFEEL, a C7-C12 ester from Inolex Chemical Company of Philadelphia, Pa. C12-C15 alkyl benzoate was obtained as FINSOLV TN, a C19-C22 ester from Innospec Inc. of Newark, Del. Isononyl isononanoate was obtained as DUB ININ, a C18 ester commercially available from Stearinerie Dubois Inc. of Ciron, France.

Example II: IL-8 Assay

An IL-8 assay was performed on the compositions of Example I to investigate the release of pro-inflammatory mediators in human epithelial cells as follows.

Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm$^2$) with formulation in example 1 for 2 hours before exposure to 100 ng/mL of Tumor Necrosis Factor-α (TNFα, available from Sigma-Aldrich of St Louis, Mo.). Equivalents were incubated for 4 hours at 37° C. with maintenance medium then supernatants were analyzed for IL-8 cytokine release using commercially available kits (Upstate Biotechnology, Charlottesville, Va.). Percent Reduction in IL-8 was calculated for the compositions relative to Comparative Composition C1 (without ester):

Percent Reduction=[1−(Value$_{sample}$/Value$_{base}$)]×100 where Value$_{sample}$ was the IL-8 level of the composition tested and Value$_{base}$ was the IL-8 value of Comparative Composition C1. The results are shown in Table 3.

TABLE 3

| Composition | Ester | Change over Comparative Composition C1 (Normalized to 100) | Percent Reduction in IL-8 |
|---|---|---|---|
| Comparative Composition C1 | None | 100 | — |
| Composition 1 | 0.1% octyldodecyl neopentanoate | 77.65 | 22.35 |
| Composition 2 | 1% octyldodecyl neopentanoate | 59.43 | 40.57 |
| Composition 3 | 3% octyldodecyl neopentanoate | 57.73 | 42.27 |
| Composition 4 | 3% octyldodecyl neopentanoate | 58.73 | 41.27 |
| Composition 5 | 10% octyldodecyl neopentanoate | 86.54 | 13.46 |

While 4-hexyl resorcinol is known to provide anti-aging activity, these results indicate that 4-hexyl resorcinol-containing compositions also containing octyldodecyl neopentanoate, a high carbon chain ester, show increased IL-8 inhibition activity over compositions containing only 4-hexyl resorcinol. The anti-aging activity also generally increases with the amount of octyldodecyl neopentanoate in the composition.

Example III: IL-8 Assay

Additional IL-8 Assays were performed as described in Example II. Compositions (described in Table 2) containing 4-hexyl resorcinol with different esters, each present at 3% by weight, were compared with Composition 6 according to the invention containing 3% by weight pentaerythritol tetraethylhexanoate. The results are shown in Table 4.

TABLE 4

| Composition | Ester | Change over Comparative Composition C1 (Normalized to 100) | Percent Reduction in IL-8 |
|---|---|---|---|
| Comparative Example C1 | None | 100 | — |
| Composition 6 | 3% pentaerythritol tetraethylhexanoate | 47.64 | 52.36 |

TABLE 4-continued

| Composition | Ester | Change over Comparative Composition C1 (Normalized to 100) | Percent Reduction in IL-8 |
|---|---|---|---|
| Comparative Example C2 | 3% neopentyl glycol diheptanoate | 78.70 | 21.30 |
| Comparative Example C3 | 3% C12-C15 alkyl benzoate | 89.79 | 10.21 |
| Comparative Example C4 | 3% isononyl isonanoate | 100.95 | −0.95 |

It can be seen from the data above that esters having high carbon chains (octyldodecyl neopentanoate and pentaerythritol tetraethylhexanoate, having 25 and 37 carbons, respectively) provide a substantial boost in the activity of 4-hexyl resorcinol over compositions without these esters. Esters with lower carbon chains, neopentyl glycol diheptanoate, C12-C15 alkyl benzoate, and isononyl isonanoate (having 7-12, 19-22, and 18 carbons, respectively) provide only a modest boost or no boost at all to the activity of 4-hexyl resorcinol, even when used in relatively high concentrations.

It is understood that while the invention has been described in conjunction with the detailed description thereof, that the foregoing description is intended to illustrate and not limit the scope the invention, which is defined by the scope of the appended claims. Other aspects, advantages, and modifications are within the claims.

We claim:

1. A composition comprising
at least about 70% by weight water;
about 0.1 to about 0.4% by weight of 4-hexyl resorcinol;
about 1 to about 3% by weight of octyldodecyl neopentanoate; and
acrylates/C10-30 alkyl acrylate crosspolymer;
wherein the composition comprises less than 5% by weight oils including octyldodecyl neopentanoate and is substantially free of emulsifiers selected from the group consisting of alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, amide ethoxylates, monoglyceride ethoxylates, sorbitan ester ethoxylates, alkyl polyglycosides, polyoxyethylene derivatives of polyol esters wherein the polyoxyethylene derivative of polyol ester (1) is derived from (a) a fatty acid containing from about 8 to about 22, such as from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, such as about 20 to about 80 oxyethylene units; and (3) has an average of about 1 to about 3 fatty acid residues per mole of polyoxyethylene derivative of polyol esteralkyl glucosides, silicone emulsifiers, alkyl betaines, amidoalkyl betaines, amidoalkyl sultaines, amphophosphates, phosphorylated imidazolines, carboxyalkyl alkyl polyamines, alkylimino-dipropionates, alkylamphoglycinates (mono or di), alkylamphoprionates (mono or di), N-alkyl b-aminoproprionic acids, alkylpolyamino carboxylates, alkyl quaternaries, benzyl quaternaries, ester quaternaries, ethoxylated quaternaries, and alkyl amines.

2. A composition comprising
at least about 70% by weight water;
about 0.1 to about 0.4% by weight of 4-hexyl resorcinol;
about 1 to about 3% by weight of octyldodecyl neopentanoate;
acrylates/C10-30 alkyl acrylate crosspolymer;
cetearyl olivate;
sorbitan olivate; and
glycerin;
wherein the composition comprises less than 5% by weight oils including octyldodecyl neopentanoate.

3. The composition of claim 2 substantially free of emulsifiers selected from the group consisting of alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, amide ethoxylates, monoglyceride ethoxylates, sorbitan ester ethoxylates, alkyl polyglycosides, polyoxyethylene derivatives of polyol esters wherein the polyoxyethylene derivative of polyol ester (1) is derived from (a) a fatty acid containing from about 8 to about 22, such as from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, such as about 20 to about 80 oxyethylene units; and (3) has an average of about 1 to about 3 fatty acid residues per mole of polyoxyethylene derivative of polyol esteralkyl glucosides, silicone emulsifiers, alkyl betaines, amidoalkyl betaines, amidoalkyl sultaines, amphophosphates, phosphorylated imidazolines, carboxyalkyl alkyl polyamines, alkylimino-dipropionates, alkylamphoglycinates (mono or di), alkylamphoprionates (mono or di), N-alkyl b-aminoproprionic acids, alkylpolyamino carboxylates, alkyl quaternaries, benzyl quaternaries, ester quaternaries, ethoxylated quaternaries, and alkyl amines.

\* \* \* \* \*